(12) United States Patent
Reardon

(10) Patent No.: US 12,390,296 B2
(45) Date of Patent: Aug. 19, 2025

(54) ROBOTIC SURGICAL SYSTEMS AND DRAPES FOR COVERING COMPONENTS OF ROBOTIC SURGICAL SYSTEMS

(71) Applicant: Covidien LP, Mansfield, MA (US)

(72) Inventor: Shane Reardon, Branford, CT (US)

(73) Assignee: Covidien LP, Mansfield, MA (US)

( * ) Notice: Subject to any disclaimer, the term of this patent is extended or adjusted under 35 U.S.C. 154(b) by 561 days.

(21) Appl. No.: 17/631,736

(22) PCT Filed: Aug. 25, 2020

(86) PCT No.: PCT/US2020/047779
§ 371 (c)(1),
(2) Date: Jan. 31, 2022

(87) PCT Pub. No.: WO2021/041401
PCT Pub. Date: Mar. 4, 2021

(65) Prior Publication Data
US 2022/0273387 A1    Sep. 1, 2022

Related U.S. Application Data

(60) Provisional application No. 62/892,626, filed on Aug. 28, 2019.

(51) Int. Cl.
*A61B 46/10*     (2016.01)
*A61B 34/00*     (2016.01)
(Continued)

(52) U.S. Cl.
CPC .............. *A61B 46/10* (2016.02); *A61B 34/37* (2016.02); *A61B 34/74* (2016.02); *A61B 46/40* (2016.02)

(58) Field of Classification Search
None
See application file for complete search history.

(56) References Cited

U.S. PATENT DOCUMENTS 5,522,403 A * 6/1996 Bark ...................... A61B 90/40
 128/853
5,970,980 A * 10/1999 Adair ...................... H04N 5/64
 128/849
(Continued)

FOREIGN PATENT DOCUMENTS

CN     106232049 A    12/2016
EP      0788777 A1    8/1997
(Continued)

OTHER PUBLICATIONS

International Search report dated Dec. 7, 2020, issued in corresponding international appln. no. PCT/US2020/047779, 8 pages.
(Continued)

*Primary Examiner* — Carl H Layno
*Assistant Examiner* — Manolis Pahakis
(74) *Attorney, Agent, or Firm* — Carter, DeLuca & Farrell LLP

(57) ABSTRACT

A drape for covering a robotic surgical system includes a proximal section joined to and continuous with a distal section. The distal section is fabricated from a relatively strong material and is configured to cover the more dynamic portions of the robotic surgical system, and the proximal section is fabricated from a light-permeable material and is configured to cover the more static portions of the robotic surgical system.

20 Claims, 5 Drawing Sheets

(51) Int. Cl.
*A61B 34/37* (2016.01)
*A61B 46/00* (2016.01)

(56) References Cited

U.S. PATENT DOCUMENTS

| | | | |
|---|---|---|---|
| 6,132,368 A | 10/2000 | Cooper | |
| 7,666,191 B2* | 2/2010 | Orban, III | A61B 46/10 606/1 |
| 7,699,855 B2* | 4/2010 | Anderson | A61B 34/30 606/1 |
| 7,886,743 B2* | 2/2011 | Cooper | A61B 46/10 606/130 |
| 8,042,549 B2 | 10/2011 | Kaska | |
| 10,357,324 B2* | 7/2019 | Flatt | A61B 46/10 |
| 10,932,877 B2* | 3/2021 | Devengenzo | A61B 46/10 |
| 11,033,178 B2* | 6/2021 | Polayes | A61B 8/4281 |
| 11,364,021 B2* | 6/2022 | Robinson | A61B 10/0233 |
| 11,510,747 B2* | 11/2022 | Zemlok | A61B 34/30 |
| 2007/0239172 A1* | 10/2007 | Lee | A61B 34/71 606/130 |
| 2012/0298116 A1* | 11/2012 | Haines | A61B 46/00 128/853 |
| 2014/0338676 A1* | 11/2014 | Marinchak | A61B 46/10 128/855 |
| 2015/0202009 A1* | 7/2015 | Nussbaumer | A61B 46/10 128/856 |
| 2016/0278738 A1 | 9/2016 | Buchalter | |
| 2019/0000580 A1 | 1/2019 | Scheib et al. | |

FOREIGN PATENT DOCUMENTS

| | | |
|---|---|---|
| WO | 2012161869 A1 | 11/2012 |
| WO | 2015110542 A1 | 7/2015 |
| WO | 2018217430 A1 | 11/2018 |
| WO | 2019032986 A1 | 2/2019 |
| WO | 2019036004 A1 | 2/2019 |

OTHER PUBLICATIONS

Extended European Sear Report for European Patent Application No. 20856161.3 dated Aug. 21, 2023 (8 pages).
Chinese Office Action issued in corresponding Chinese Application No. 202080057905.6 dated Mar. 28, 2025, 14 pages.

* cited by examiner

ROBOTIC SURGICAL SYSTEMS AND DRAPES FOR COVERING COMPONENTS OF ROBOTIC SURGICAL SYSTEMS

The present application is a U.S. National Stage Application filed under 35 U.S.C. § 371 (a) claiming the benefit of and priority to International Patent Application No. PCT/US2020/047779, filed Aug. 25, 2020, which claims the benefit of and priority to U.S. Provisional Patent Application No. 62/892,626, filed Aug. 28, 2019, the entire disclosures of each of which being incorporated by reference herein.

BACKGROUND

Robotic surgical systems have been used in minimally invasive medical procedures. Some robotic surgical systems include a console supporting a surgical robotic arm and a surgical instrument, having at least one end effector (e.g., forceps or a grasping tool), mounted to the surgical robotic arm. The surgical robotic arm provides mechanical power to the surgical instrument for its operation and movement.

In robotic assisted medical procedures, the various components of a robotic surgical system are generally draped to decrease the probability of inadvertent contamination of an external surgical sterile field. Accordingly, it would be beneficial to provide a means for more easily deploying a drape while decreasing the probability of inadvertent contamination of the external surgical sterile field.

SUMMARY

In accordance with an aspect of the present disclosure, a drape for covering a robotic surgical system is provided. The drape includes a proximal section and a distal section each defining a cavity therein. The cavity of the proximal section is dimensioned for receipt of at least a base portion of a surgical robotic arm, and the cavity of the distal section is dimensioned for receipt a surgical assembly, which is coupled to the surgical robotic arm. The proximal section is fabricated from a first material, and the distal section is fabricated from a second material that is stronger than the first material. The proximal and distal sections are joined to one another, such that the cavity of the proximal section is contiguous with the cavity of the distal section.

In aspects, the first material may be diaphanous and the second material may be opaque.

In some aspects, the first material may be low density polyethylene and the second material may be polyurethane and/or ethylene methyl acrylate.

In further aspects, the proximal and distal sections may be joined to one another via a medical grade adhesive.

In other aspects, the proximal section may have an open and tubular distal end, and the distal section may have an open and tubular proximal end overlapping the distal end of the proximal section.

In aspects, the proximal and distal sections may be joined to one another at their respective distal and proximal ends.

In some aspects, the first material may be thinner than the second material.

In further aspects, the second material may have a greater tensile strength, tear resistance, and puncture resistance relative to the first material.

In other aspects, the first material may be more permeable to light than the second material.

In aspects, the distal section may have a first region and a second region extending from the first region. The first region may be configured to cover a plurality of movable arms of the surgical robotic arm, and the second region may be configured to cover an instrument drive unit and a slide of the surgical assembly.

In some aspects, the first region may have a greater diameter than the second region.

In accordance with another aspect of the present disclosure, a robotic surgical system is provided and includes a surgical robotic arm, a surgical assembly, and a drape. The surgical robotic arm has a base portion and a plurality of movable members coupled to the base portion. The surgical assembly is coupled to a first movable member of the plurality of movable members of the surgical robotic arm. The drape includes a proximal section and a distal section joined to the proximal section and each defining a cavity therein. The cavity of the proximal section is dimensioned for receipt of the base portion of the surgical robotic arm, and the cavity of the distal section is dimensioned for receipt of the surgical assembly and the movable members of the surgical robotic arm. The proximal section is fabricated from a first material, and the distal section is fabricated from a second material, different than the first material.

In aspects, the cavity of the proximal section may be contiguous with the cavity of the distal section.

Further details and aspects of exemplary embodiments of the present disclosure are described in more detail below with reference to the appended figures.

As used herein, the terms parallel and perpendicular are understood to include relative configurations that are substantially parallel and substantially perpendicular up to about plus or minus 10 degrees from true parallel and true perpendicular.

BRIEF DESCRIPTION OF THE DRAWINGS

Embodiments of the present disclosure are described herein with reference to the accompanying drawings, wherein.

DETAILED DESCRIPTION

Figure 1:
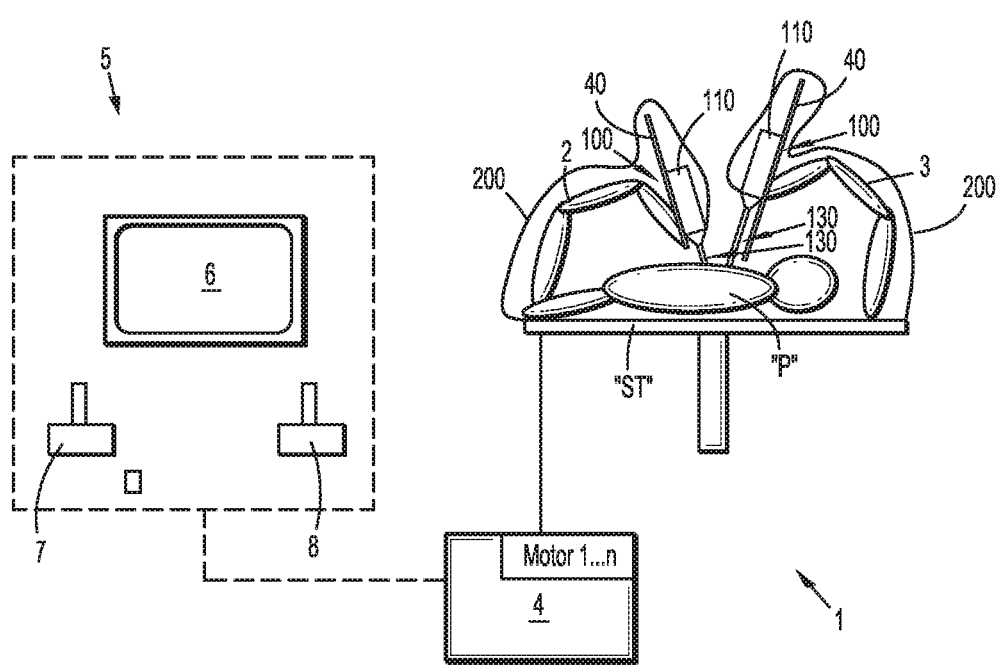
FIG. 1 is a schematic illustration of a robotic surgical system including a surgical robotic arm, a robotic surgical assembly coupled to the robotic arm, and a drape covering the surgical robotic arm and the robotic surgical assembly.

Embodiments of the presently disclosed robotic surgical system including a surgical robotic arm, a surgical assembly (including an instrument drive unit ("IDU") and a surgical instrument), and a drape for covering some or all of the aforementioned components, are described in detail with reference to the drawings, in which like reference numerals designate identical or corresponding elements in each of the several views. As used herein the term "distal" refers to that portion of the surgical robotic arm, surgical assembly, or drape, that is closer to the patient, while the term "proximal" refers to that portion of the surgical robotic arm, surgical assembly, or drape, that is farther from the patient.

As will be described in detail below, provided is a sterile, disposable or reusable drape for covering various components of a robotic surgical system. The drape maintains sterility of the surgical assembly and surgical robotic arm disposed therein. The drape may also protect the robotic surgical system from liquid and particle ingress that may otherwise harm the system. The drape is manufactured by joining two separate sheets of material via an adhesive or any other suitable type of connection. The two sheets of material each exhibit unique material properties making each suitable for covering particular sections of the robotic surgical system.

Figure 2:
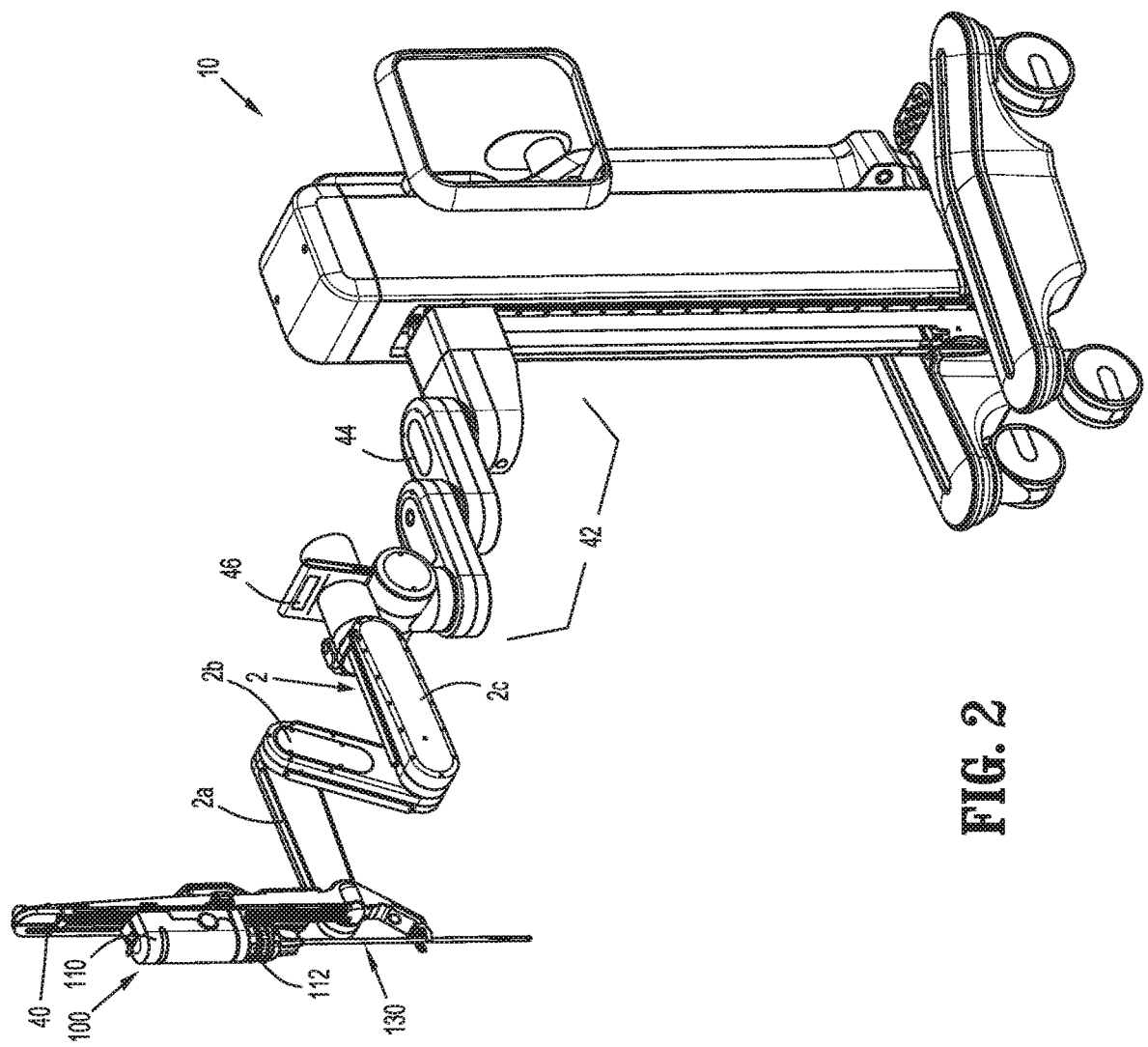
FIG. 2 is a perspective view illustrating the robotic surgical assembly and the robotic arm of FIG. 1 attached to a robotic arm cart.
Figure 3:
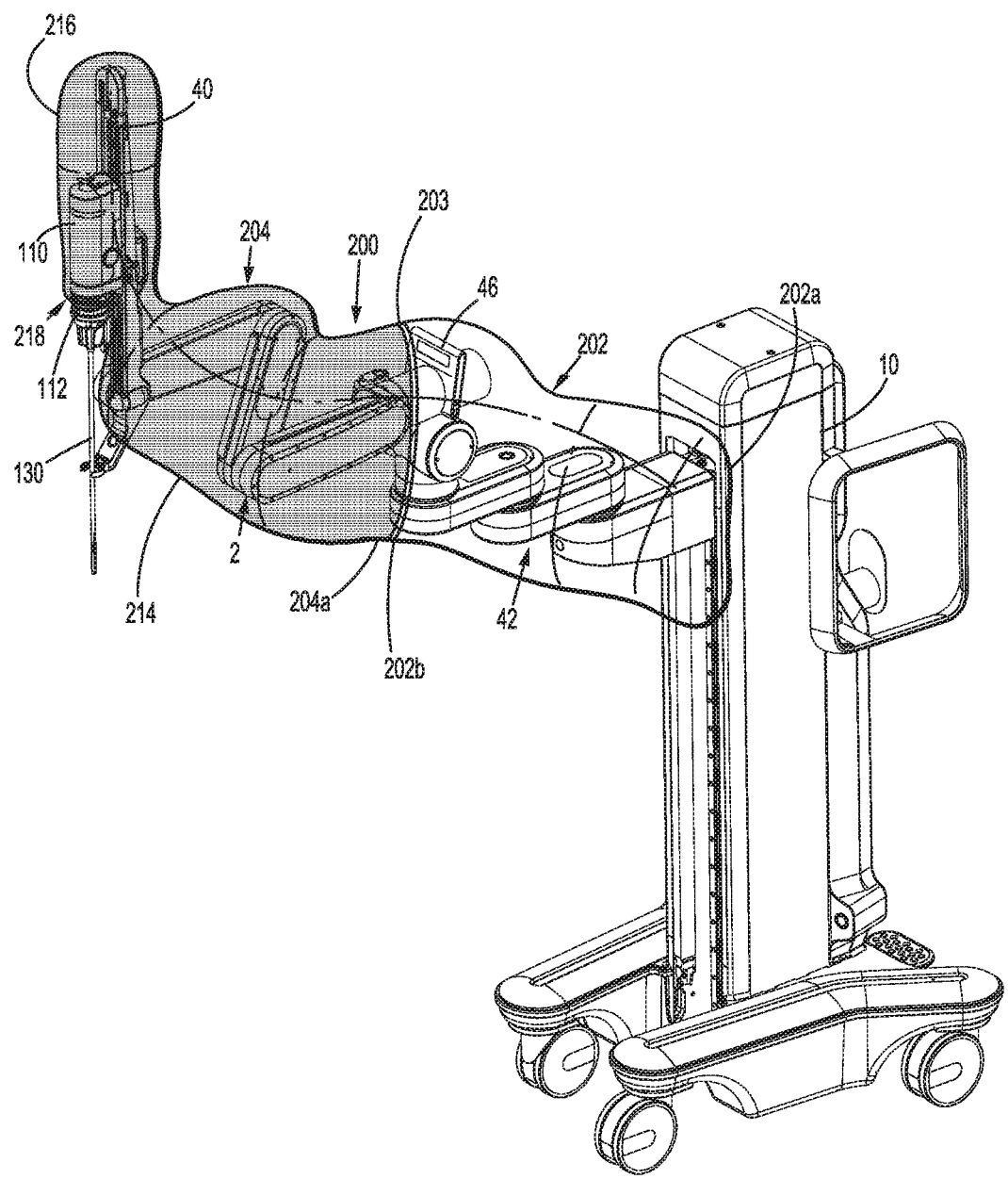
FIG. 3 is a perspective view illustrating the robotic surgical assembly and the robotic arm of FIG. 2 covered in the drape of FIG. 1.

Referring initially to FIGS. 1-3, a surgical system, such as, for example, a robotic surgical system 1, generally includes a robotic arm or robotic arms 2, 3 coupled to a robotic cart 10, a surgical assembly 100 coupled to the surgical robotic arm 2, and a drape 200 for covering the robotic arm 2 and the surgical assembly 100. In some embodiments, the drape 200 may be dimensioned to also cover the robotic arm cart 10. The surgical assembly 100 includes an instrument drive unit (hereinafter "IDU") 110 coupled to a slide rail 40 of surgical robotic arms 2, 3, and an electromechanical surgical instrument 130 operably coupled to IDU 110 by a sterile interface module 112 of surgical assembly 100.

The surgical system 1 further includes a control device 4 and an operating console 5 coupled with control device 4. Operating console 5 includes a display device 6, which is set up in particular to display three-dimensional images; and manual input devices 7, 8, by means of which a person (not shown), for example a surgeon, is able to telemanipulate robotic arms 2, 3 in a first operating mode, as known in principle to a person skilled in the art. Each of the robotic arms 2, 3 may be composed of a plurality of members 2a, 2b, 2c, which are connected through joints. The first member 2a couples to the surgical assembly 100 and the third member 2c couples to a base portion 42 of the surgical robotic arm 2. The base portion 42 may include a plurality of pivotable arms 44 configured to detachably couple to the cart 10, and a display screen 46 coupled to one of the pivotable arms 44.

Robotic arms 2, 3 may be driven by electric drives (not shown) that are connected to control device 4. Control device 4 (e.g., a computer) may be set up to activate the drives, in particular by means of a computer program, in such a way that robotic arms 2, 3, the attached robotic surgical assembly 100, and thus electromechanical surgical instrument 130 (including an electromechanical end effector (not shown)) execute a desired movement according to a movement defined by means of manual input devices 7, 8. Control device 4 may also be set up in such a way that it regulates the movement of robotic arms 2, 3.

Robotic surgical system 1 is configured for use on a patient "P" lying on a surgical table "ST" to be treated in a minimally invasive manner by means of a surgical instrument, e.g., electromechanical surgical instrument 130. In embodiments, robotic arms 2, 3 may be coupled to robotic arm cart 10 (FIG. 2) rather than surgical table "ST." Robotic surgical system 1 may also include more than two robotic arms 2, 3, the additional robotic arms likewise being connected to control device 4 and being telemanipulatable by means of operating console 5. A surgical instrument, for example, electromechanical surgical instrument 130 (including the electromechanical end effector), may also be attached to the additional robotic arm.

Control device 4 may control a plurality of motors, e.g., motors (Motor 1 . . . n), with each motor configured to drive movement of robotic arms 2, 3 in a plurality of directions. Further, control device 4 may control a motor assembly (not explicitly shown) of IDU 110 of robotic surgical assembly 100 that drives various operations of surgical instrument 130. In embodiments, each motor of the IDU 110 can be configured to actuate a drive rod/cable or a lever arm to effect operation and/or movement of electromechanical surgical instrument 130.

For a detailed discussion of the construction and operation of a robotic surgical system, reference may be made to U.S. Pat. No. 8,828,023, entitled "Medical Workstation," the entire contents of which are incorporated by reference herein.

Figure 4:
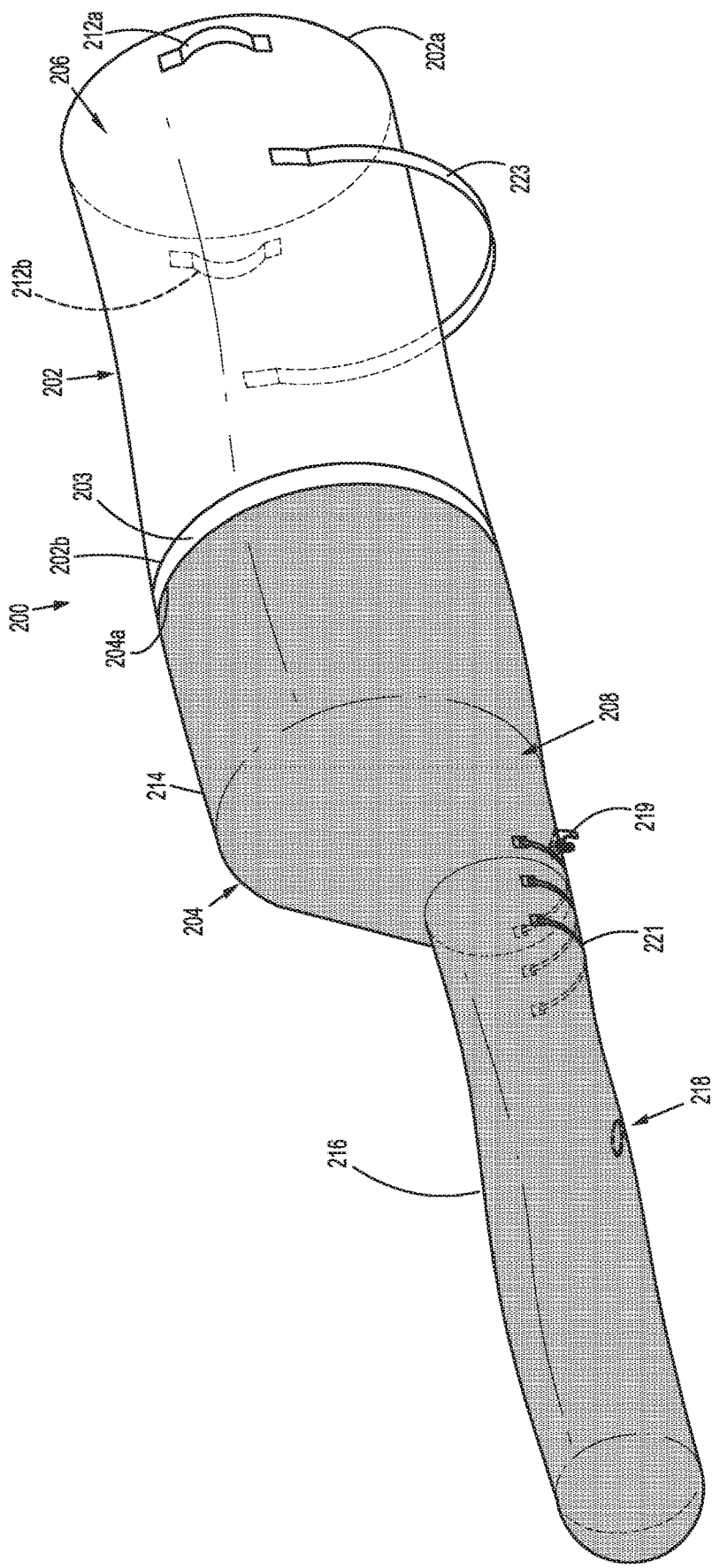
FIG. 4 is a perspective view illustrating the drape of FIG. 3.
Figure 5:
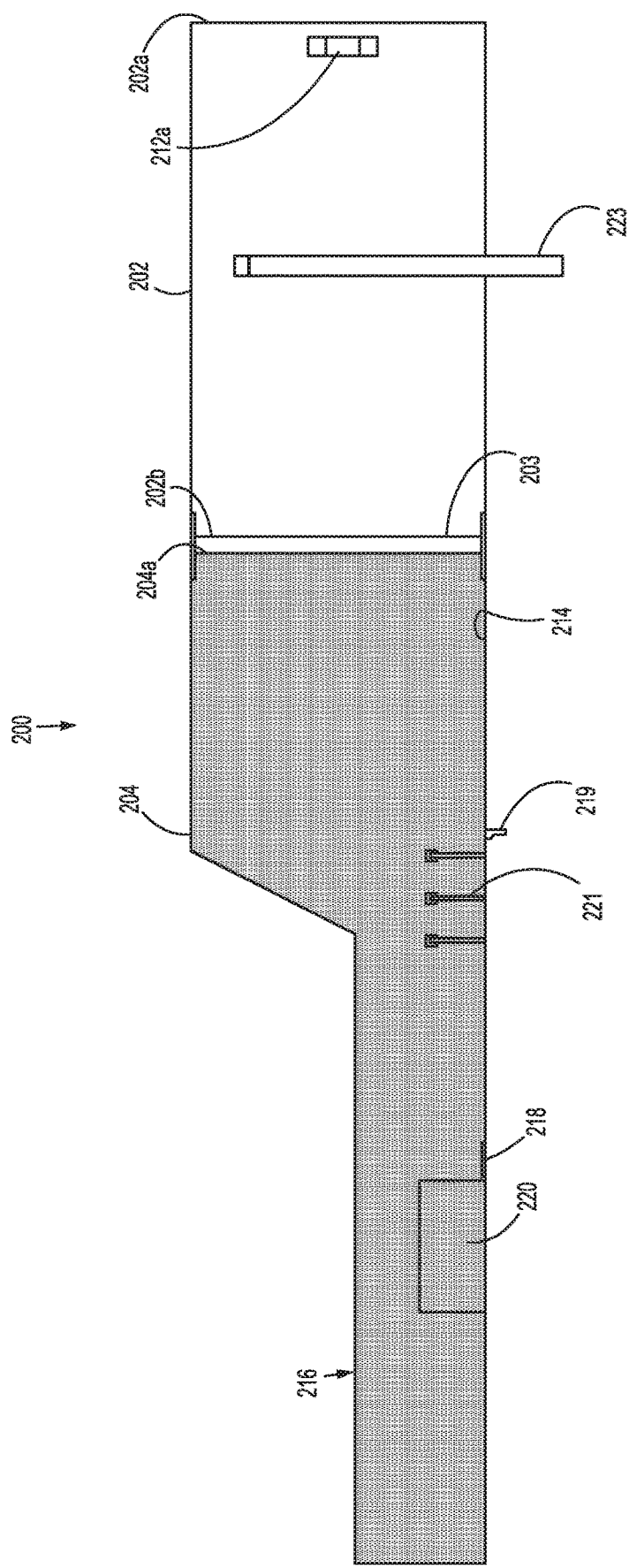
FIG. 5 is a side view illustrating the drape of FIG. 4.

With reference to FIGS. 3-5, the drape 200 of the robotic surgical system 1 has a generally elongated configuration, such as, for example, a tubular shape, and generally includes a proximal section 202 configured to cover the static portions of the surgical robotic system 1 and a distal section 204 configured to cover the more dynamic portions of the surgical robotic system 1. The proximal section 202 of the drape 200 has a tubular shape and defines an elongated cavity 206 therein dimensioned for receipt of the base portion 42 of the surgical robotic arm 2 (including the arms 44 and the display 46). The proximal section 202 is fabricated from a first material that is diaphanous to provide a clear view of the components (e.g., display 46) of the surgical robotic system 1 covered by the proximal section 202. An exemplary material for the proximal section 202 may be low density polyethylene, which is light-permeable and fluid-resistant. In other aspects, the first material of the proximal section 202 may be high-density polyethylene (HDPE), polypropylene, and/or polyethylene materials or other similar non-toxic, biocompatible compounds.

The proximal section 202 may have a pair of handles 212a, 212b for guiding the drape 200 over the surgical robotic system 1. The handles 212a, 212b may be affixed to any suitable location of the drape 200. The proximal section 202 of the drape 200 has an open proximal end 202a and an open distal end 202b joined to or otherwise coupled with an open proximal end 204a of the distal section 204.

The distal section 204 of the drape 200 has a tubular shape and defines an elongated cavity 208 therein dimensioned for receipt of the members 2a, 2b, 2c of the surgical robotic arm 2 and the surgical assembly 100 (including the instrument drive unit 110 and the slide 40). The distal section 204 is fabricated from a second material, different than the first material of the proximal section 202. Since the distal section 204 is configured to cover the more dynamic portions of the robotic surgical system 1 (e.g., the movable arms 2a, 2b, 2c and the IDU 110), a stronger material is selected for the distal section 204 compared to the proximal section 202. Exemplary materials for the distal section 204 are polyurethane and/or ethylene methyl acrylate; however, other suitable materials are also contemplated. The material from which the distal section 204 is fabricated is more resistant to tearing and puncture and exhibits greater tensile strength than the material from which the proximal section 202 is fabricated. Depending on the material used to form the distal section 204, it may be opaque and therefore less translucent compared to the proximal section 202.

Due to the proximal and distal sections 202, 204 being fabricated from two different materials with each possibly having a different melting temperature, joining the proximal and distal sections 202, 204 using heat sealing may be challenging. Accordingly, the open and tubular distal end 202b of the proximal section 202 and the open and tubular proximal end 204a of the distal section 204 may be bonded, joined, or otherwise coupled to one another using a medical grade adhesive, such as, for example, acrylic, cyanoacrylate, and/or epoxy. The proximal end 204a of the distal section 204 may be disposed around the distal end 202*b* of the proximal section 202 or the distal end 202*b* of the proximal section 202 may be disposed around the proximal end 204*a* of the distal section 204 and then joined to one another. In some aspects, the proximal and distal sections 202, 204 may be joined using any suitable fastening mechanism, such as, for example, glue, thermally bonds, ultrasonically welds, stitches, hook and loop fasteners, or seam bonds.

The distal section 204 includes a first region 214 coupled to the proximal section 202 and a second region 216 coupled to (e.g., via heat sealing) and extending distally from the first region 214. The first region 214 has a first diameter configured to surround the movable members 2*a*, 2*b*, 2*c* of the surgical robotic arm 2 and a length sufficient to accommodate the members 2*a*, 2*b*, 2*c* in a fully extended position. The second region 216 has a second diameter, less than the first diameter of the first region 214, and is configured to surround the instrument drive unit 110 and the slide 40. The second region 216 may terminate at a closed distal-most end.

The second region 216 may have a reinforcement patch 220 (FIG. 5) disposed at a location where the instrument drive unit 110 is intended to be when the drape 200 is covering the robotic surgical system 1. The second region 216 defines an inlet or channel 218 in fluid communication with the cavity 206 of the proximal section 202. The inlet 218 has a generally annular shape dimensioned to form a fluid-tight seal with the sterile interface module 112 (FIG. 3) of the surgical assembly 100. In some aspects, the inlet 218 may be dimensioned to form a fluid tight seal with a distal end portion of the instrument drive unit 110 when the sterile interface module 112 is not used. Reinforcement patch 220 may be located distal of inlet 218 and/or substantially midway along a length of second region 216.

It is contemplated that the first material of first region 214 of drape 200 may be relatively thinner than the second material of second region 216 of drape 200. It is further contemplated that the second material of second region 216 of drape 200 may have a relatively greater tensile strength, tear resistance and/or puncture resistance as compared to the first material of first region 214 of drape 200.

During assembly, the drape 200 is placed over the rail 40 and the instrument drive unit 110 using the handles 212*a*, 212*b* to guide the drape 200 over the robotic surgical system 1. The proximal section 202 of the drape 200 is guided over the base portion 42 of the surgical robotic arm 2 and the seal 203 between the proximal and distal sections 202, 204 is disposed distally (e.g., in front of) the display 46. The first region 214 of the distal section 204 is positioned over the movable members 2*a*, 2*b*, 2*c* of the robotic arm 2 and the second region 216 of the distal section 204 is positioned over the slide 40 and the instrument drive unit 110. The sterile interface module 112 is positioned to extend through the inlet 218 of the distal section 204 of the drape 200 with the surgical instrument 130 protruding from the drape 200. A latch 219, flexible strips 221, ties 223, clips, straps, or any other suitable fasteners may be used to attach selected sections of the drape 200 to the robotic surgical system 1 to ensure the drape 200 is maintained in position.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

The invention claimed is:

1. A drape for covering a robotic surgical system, the drape comprising:

a proximal section defining a cavity therein dimensioned for receipt of at least a base portion of a surgical robotic arm, the proximal section being fabricated from a first material, the proximal section being tubular and defining a first diameter; and a distal section defining a cavity therein dimensioned for receipt of a surgical assembly that is coupled to the surgical robotic arm, the distal section being fabricated from a second material, stronger than the first material, wherein the proximal and distal sections are joined to one another, such that the cavity of the proximal section is contiguous with the cavity of the distal section, the distal section being tubular and including:

a first region having a diameter equal to the first diameter of the proximal section;

a second region integral with and extending distally from the first region, the second region defining a second diameter which is smaller than the first diameter; and an inlet formed in a side wall of the second region of the distal section and being in fluid communication with the cavity of the distal section, wherein the surgical assembly is connected to the surgical robotic arm through the inlet such that the surgical assembly is located externally of the second region of the distal section and the surgical robotic arm is located internally of the second region of the distal section.

2. The drape according to claim 1, wherein the first material is diaphanous and the second material is opaque.

3. The drape according to claim 1, wherein the first material is low density polyethylene and the second material is at least one of polyurethane or ethylene methyl acrylate.

4. The drape according to claim 1, wherein the proximal and distal sections are joined to one another via a medical grade adhesive.

5. The drape according to claim 1, wherein the proximal section has an open and tubular distal end, and the distal section has an open and tubular proximal end overlapping the distal end of the proximal section.

6. The drape according to claim 5, wherein the proximal and distal sections are joined to one another at their respective distal and proximal ends.

7. The drape according to claim 1, wherein the first material is thinner than the second material.

8. The drape according to claim 1, wherein the second material has a greater tensile strength, tear resistance, and puncture resistance relative to the first material.

9. The drape according to claim 1, wherein the first material is more permeable to light than the second material.

10. The drape according to claim 1, wherein the first region of the distal section is configured to cover a plurality of movable arms of the surgical robotic arm, and the second region of the distal section is configured to cover an instrument drive unit and a slide of the surgical assembly.

11. The drape according to claim 1, wherein the distal section includes a latch supported thereon and extending outwardly therefrom.

12. The drape according to claim 11, wherein the latch is supported on the first region of the distal section.

13. The drape according to claim 11, wherein the latch includes a pair of fingers.

14. The drape according to claim 1, wherein the proximal section defines a first central longitudinal axis, and wherein the second region of the distal section defines a second central longitudinal axis, wherein the second central longitudinal axis extends parallel to the first central longitudinal axis and is spaced a radial distance from the first central longitudinal axis.

15. A drape for covering a robotic surgical system, the drape comprising:
- a proximal section defining a cavity therein dimensioned for receipt of at least a base portion of a surgical robotic arm, the proximal section being fabricated from a first material, the proximal section being tubular and defining a first diameter and a first central longitudinal axis; and
- a distal section defining a cavity therein dimensioned for receipt of a surgical assembly that is coupled to the surgical robotic arm, the distal section being fabricated from a second material, stronger than the first material, wherein the proximal and distal sections are joined to one another, such that the cavity of the proximal section is contiguous with the cavity of the distal section, the distal section being tubular and including:
  - a first region having a diameter equal to the first diameter of the proximal section;
  - a second region integral with and extending distally from the first region, the second region defining a second diameter and a second central longitudinal axis, wherein the second central longitudinal axis extends parallel to the first central longitudinal axis and is spaced a radial distance from the first central longitudinal axis; and
  - an inlet formed in a side wall of the second region of the distal section and being in fluid communication with the cavity of the distal section, wherein the surgical assembly is connected to the surgical robotic arm through the inlet such that the surgical assembly is located externally of the second region of the distal section and the surgical robotic arm is located internally of the second region of the distal section.

16. The drape according to claim 15, wherein the proximal section has an open and tubular distal end, and the distal section has an open and tubular proximal end overlapping the distal end of the proximal section.

17. The drape according to claim 15, wherein the distal section includes a latch supported thereon and extending outwardly therefrom.

18. The drape according to claim 17, wherein the latch is supported on the first region of the distal section.

19. The drape according to claim 17, wherein the latch includes a pair of fingers.

20. The drape according to claim 15, wherein the second region of the distal section defines a second diameter which is smaller than the first diameter of the proximal section.

* * * * *